United States Patent [19]
Ireland et al.

[11] Patent Number: 5,830,996
[45] Date of Patent: Nov. 3, 1998

[54] CYCLIC PEPTIDE ANTITUMOR AGENT FROM AN ASCIDIAN

[75] Inventors: Chris M. Ireland, Sandy, Utah; Annette Fernandez, Philadelphia, Pa.

[73] Assignee: University of Utah Research Foundation, Salt Lake City, Utah

[21] Appl. No.: 722,658

[22] Filed: Sep. 27, 1996

[51] Int. Cl.[6] .............................. A61K 38/00; C07K 5/00; C07K 7/00

[52] U.S. Cl. .............................. 530/323; 530/317; 514/9; 514/10; 514/21

[58] Field of Search ................................ 530/317, 323; 514/9, 10, 21

[56] References Cited

U.S. PATENT DOCUMENTS

4,948,791  8/1990  Rinehart, Jr. et al. ................... 514/183

Primary Examiner—Nathan M. Nutter
Attorney, Agent, or Firm—Thorpe, North & Western L.L.P.

[57] ABSTRACT

A purified bicyclic depsipeptide, vitilevuamide, from the ascidians *Didemnum cuculliferum* and *Polysyncraton lithostrotum* is disclosed. Vitilevuamide has antitumor activity as demonstrated by standard in vitro and in vivo assays. An anticancer composition is also disclosed, comprising an effective amount of vitilevuamide and an inert carrier. A method of treating cancer is also disclosed, comprising administering an anticancer composition comprising an effective amount of vitilevuamide and an inert carrier.

17 Claims, 5 Drawing Sheets

CYCLIC PEPTIDE ANTITUMOR AGENT FROM AN ASCIDIAN

BACKGROUND OF THE INVENTION

This invention relates to a composition and method of use thereof for treating cancer. More particularly, the invention relates to a bicyclic depsipeptide, vitilevuamide, which has anticancer activity, and a method of use thereof for treating cancer in an individual in need thereof.

Marine organisms, especially invertebrates such as ascidians, sponges, soft corals, and mollusks, produce many secondary metabolites that are not found in the terrestrial world. Recent studies in the field of marine natural products have focused on detection of biomedically important compounds. This research has resulted in the discovery of compounds that have anticancer, antiviral, and antiinflammatory activity. CNS membrane-active toxins, ion channel effectors, and metabolites that interact with DNA and microfilament processes have also been identified.

Each phylum produces a characteristic distribution of compounds. For example, in the years 1977 to 1985, 85% of the metabolites isolated from coelenterates were terpenoids; 37% and 41% of compounds isolated from sponges were terpenoids and nitrogenous metabolites, respectively; and 89% of compounds isolated from ascidians were nitrogenous compounds, such as amino acid derivatives. C. M. Ireland et al., 13 Proc. Calif. Acad. Sci. 41 (1987).

The birth of the field of marine natural products was marked with the isolation of several modified arabino nucleosides from the sponge, *Cryptoethya crypta*. W. Bergann & R. J. Feeney, 72 J. Am. Chem. Soc. 2809 (1950). The first ascidian metabolite, geranyl hydroquinone, was isolated in 1974 from Aplidium sp. W. Fenical, 1974 Food-Drugs Sea 388 (1976). This compound exhibited activity against some forms of leukemia, Rous sarcoma, and mammary carcinoma in test animals. Since then, ascidians have been targeted for the specific purpose of isolating compounds of biomedical importance. Between 1988 and 1992, about 165 new ascidian metabolites were discovered. C. M. Ireland et al., in D. G. Fautin ed., 13 Biomedical Importance of Marine Organisms 41 (1988).

Peptides are one of the major structural classes of compounds isolated from ascidians. Ulicylamide and ulithiacyclamide were the first of a series of cyclic peptides isolated from *Lissoclinum patella*. C. M. Ireland & P. J. Scheuer, 102 J. Am. Chem. Soc. 5688 (1980). The genus Lissoclinum has proven to be a prolific producer of two classes of cyclic peptides, the heptapeptide lissoclinamides and the octapeptide patellamides/ulithiacyclamides. Each of these classes is characterized by the presence of thiazole and oxazoline amino acids. These peptides exhibit in vitro toxin activity, with the presence of the oxazoline ring proving important to their potency. T. Shioiri et al., 36 Biochem. Pharmacol. 4181 (1987).

The first metabolite from an ascidian to enter phase III clinical trials was didemnin B, a cyclic depsipeptide isolated from the Caribbean ascidian, *Trididemnum solidum*. K. L. Rinehart et al., 212 Am. Chem. Soc. 933 (1981); K. L. Rinehart et al., 212 Science 933 (1981). Didemnins A, B, and C were first isolated in 1981 and were proposed to contain the unique structural unit, hydroxyisovalerylpropionate (HIP), and a new allo stereoisomer of statine. K. L. Rinehart et al., 109 J. Am. Chem. Soc. 6846 (1987). These didemnins were found to inhibit Herpes simplex viruses I and II, Rift Valley Fever virus, Venezuelan equine encephalitis virus, and yellow fever virus. Didemnin H, A. Boulanger et al., 35 Tetrahedron Lett. 4345 (1994), was found to interact with DNA. J. M. Pezzuto et al., 54 J. Nat'l Prod. 1522 (1991).

Cancer is the leading cause of death in many countries. In the United States and Canada, only diseases of the heart and blood vessels kill more people. About 100 kinds of cancer attack human beings. Drug therapy or chemotherapy is an important method of treating such cancers. More than 50 drugs are used against a variety of cancers, and such drugs have proven especially effective in treating leukemia and lymphoma. Anticancer drugs are designed to destroy cancer cells with as little injury to normal cells as possible. Nevertheless, the drugs tend to injure normal cells to some degree and thus produce various undesirable side effects, ranging from nausea to high blood pressure. There is a need to develop new anticancer drugs that are effective against various kinds of cancers and that are less harmful to normal cells.

In view of the foregoing, it will be appreciated that providing a new antitumor drug and a method of use thereof for treating cancerous tumors would be a significant advancement in the art.

BRIEF SUMMARY OF THE INVENTION

It is an object of the present invention to provide a new anticancer drug.

It is another object of the invention to provide a method of treating cancer in a person in need thereof.

It is also an object of the invention to provide a method of purifying vitilevuamide.

These and other objects can be achieved by providing a purified compound selected from the group consisting of vitilevuamide and pharmaceutically acceptable salts thereof. Preferably, the purified compound is vitilevuamide.

A composition for treating cancer comprises an effective amount of an anticancer agent selected from the group consisting of vitilevuamide, pharmaceutically acceptable salts thereof, and mixtures thereof; and an inert carrier. Preferably, the anticancer agent is vitilevuamide. The composition can also further comprise a member selected from the group consisting of excipients, wetting agents, emulsifying agents, and buffers.

A method for purifying vitilevuamide comprises the steps of:

(a) collecting specimens of an ascidian selected from the group consisting of *Didemnum cuculliferum* and *Polysyncraton lithostrotum*;

(b) repeatedly extracting the specimens with methanol to yield a crude homogenate;

(c) separating the crude homogenate into fractions of increasing polarity by extracting first with hexanes and then with chloroform to yield a chloroform extract;

(d) subjecting the chloroform extract to a first silica gel flash chromatography step with stepped gradient elution with chloroform, 99:1 chloroform/methanol, and then 98:2 chloroform/methanol to obtain a 98:2 chloroform/methanol eluant;

(e) subjecting the 98:2 chloroform/methanol eluant to a second silica gel flash chromatography step with stepped gradient elution with 3:7 acetone/hexanes, and then 7:3 acetone/hexanes to yield a 7:3 acetone/hexanes fraction; and (f) subjecting the 7:3 acetone/hexanes fraction to reverse phase HPLC with a mobile phase of 9:1 $CH_3CN/H_2O$ such that a fraction is separated therefrom comprising a bicyclic peptide with a molecular weight of about 1603.8.

Another method for purifying vitilevuamide comprises the steps of:

(a) collecting specimens of an ascidian selected from the group consisting of *Didemnum cuculliferum* and *Polysyncraton lithostrotum*;

(b) repeatedly extracting the specimens with methanol to yield a crude homogenate;

(c) separating the crude homogenate into fractions of increasing polarity by extracting first with hexanes and then with chloroform to yield a chloroform extract;

(d) subjecting the chloroform extract to silica gel flash chromatography with stepped gradient elution with chloroform, 99:1 chloroform/methanol, and then 98:2 chloroform/methanol to obtain a 98:2 chloroform/methanol eluant;

(e) subjecting the 98:2 chloroform/methanol eluant to reverse phase flash chromatography with stepped gradient elution with $H_2O$, 50% methanol/$H_2O$, 70% methanol/$H_2O$, 80% methanol/$H_2O$, and 90% methanol/$H_2O$ to obtain a 90% methanol/$H_2O$ eluant; and (f) subjecting the 90% methanol/$H_2O$ eluant to amino flash chromatograph with stepped gradient elution with chloroform and then 2.5% methanol/chloroform to obtain a 2.5% methanol/chloroform eluant comprising a bicyclic peptide with a molecular weight of about 1603.8.

A method for treating cancer in an individual in need of such treatment comprises administering a composition comprising an effective amount of an anticancer agent selected from the group consisting of vitilevuamide, pharmaceutically acceptable salts thereof, and mixtures thereof; and an inert carrier. Preferably, the anticancer agent is vitilevuamide. The composition can also comprise a member selected from the group consisting of excipients, wetting agents, emulsifying agents, and buffers. The composition is preferably administered by systemic administration.

DETAILED DESCRIPTION

Before the present antitumor composition and method of use thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "an excipient" includes reference to two or more of such excipients, reference to "an emulsifying agent" includes reference to one or more of such agents, and reference to "a wetting agent" includes reference to two or more of such wetting agents.

In describing and claiming the present invention, the following terminology will be used in accordance with the definitions set out below.

As used herein, such a "pharmaceutically acceptable" component is one which is suitable for use with humans and/or animals without undue adverse side effects (such as toxicity, irritation, and allergic response) commensurate with a reasonable benefit/risk ratio.

As used herein, "effective amount" means an amount of an anticancer agent that is nontoxic but sufficient to provide the desired effect and performance against cancer cells at a reasonable benefit/risk ratio attending any medical treatment.

As used herein, "administering" and similar terms mean delivering the compound or composition to the individual being treated such that the compound or composition is capable of being circulated systemically to the parts of the body where the anticancer agent can act on cancer cells. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

EXAMPLE 1

Extraction and Isolation Procedures

Specimens of *Didemnum cuculliferum* were collected at Namenalala Island, Fiji, and kept frozen until extracted. The methanol extract of the frozen tunicate (350 grams) was repeatedly extracted with 2.5 L of methanol. The crude homogenate (reduced to 50 mL) was separated into increasing polar fractions by extracting first with hexanes (3×500 mL) and chloroform (5×500 mL) using a modified Kupchan solvent partitioning scheme, S. M. Kupchan et al., 38 J. Org. Chem. 178 (1973), hereby incorporated by reference.

The resulting 325.1 mg of chloroform extract was subjected to silica gel flash chromatography in a 2.8×46 cm column packed with 60 Å, 35–70 µm silica support. Elution was by stepped gradient elution with the following eluants: $CHCl_3$; 99:1 $CHCl_3$/MeOH; 98:2 $CHCl_3$/MeOH; 97.5:2.5 $CHCl_3$/MeOH. The active factor eluted in the 98:2 $CHCl_3$/MeOH fraction. The eluted material was subjected to a second silica gel flash chromatography step with stepped gradient elution with the following eluants: 3:7 acetone/hexanes; 7:3 acetone/hexanes; acetone.

Figure 1:
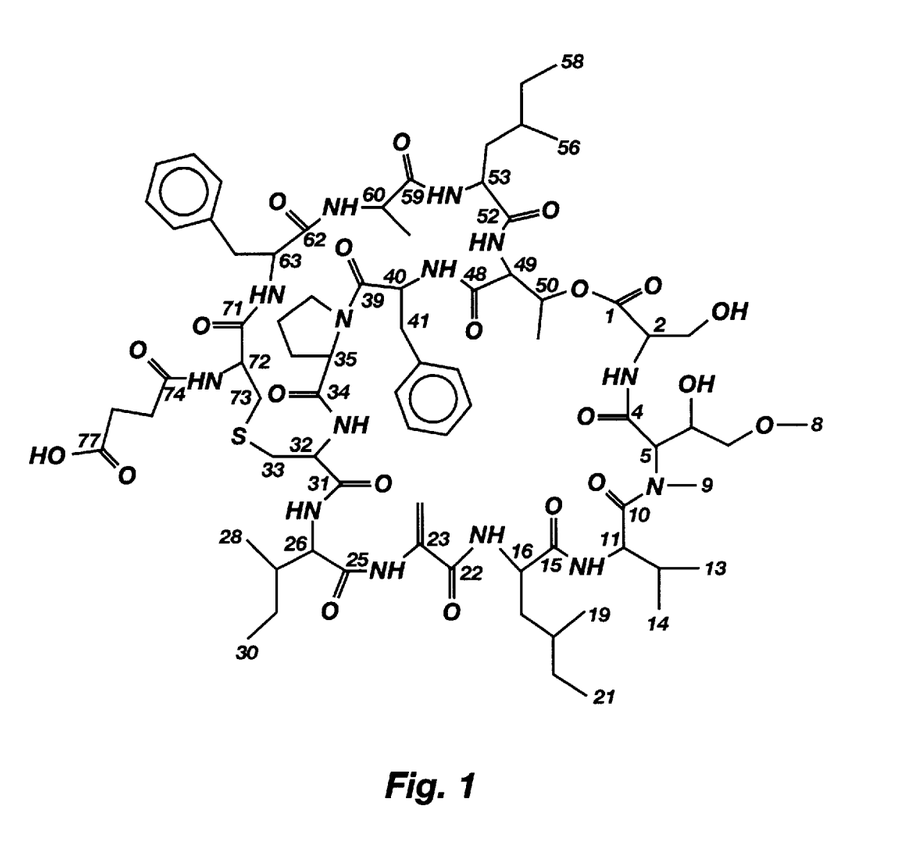
FIG. 1 shows the structure of the bicyclic depsipeptide, vitilevuamide.

The 70% acetone/hexanes fraction was subjected to reverse phase HPLC using a C-18 Rainin Microsorb 0.5×25 cm column with 100 Å, 5 µm silica gel. Elution in 90% $CH_3CN$/10% $H_2O$ and UV detection at 220 nm yielded 10.2 mg of a clear glassy compound, the new cyclic peptide vitilevuamide (FIG. 1).

EXAMPLE 2
Extraction and Isolation Procedures

Specimens of *Polysyncraton lithostrotum* were collected at Namenalala Island, Fiji, and kept frozen until extracted. The methanol extract of the frozen tunicate (350 grams) was repeatedly extracted with 2.5 L of methanol. The crude homogenate (reduced to 50 mL) was separated into increasing polar fractions by extracting first with hexanes (3×500 mL) and chloroform (5×500 mL) using a modified Kupchan solvent partitioning scheme, S. M. Kupchan et al., 38 J. Org. Chem. 178 (1973), hereby incorporated by reference.

The resulting chloroform extract was subjected to silica gel flash chromatography in a 2.8×46 cm column packed with 60 Å, 35–70 μm silica support. Elution was by stepped gradient elution with the following eluants: $CHCl_3$; 99:1 $CHCl_3$/MeOH; 98:2 $CHCl_3$/MeOH; 97.5:2.5 $CHCl_3$/MeOH. The active factor eluted in the 98:2 $CHCl_3$/MeOH fraction. Reverse phase flash chromatography was then performed (28 mm I.D.×46 mm column) with LiChroprep RP-18, 40–63 μm, using stepped gradient elution in, successively, 100% $H_2O$, 50% MeOH in $H_2O$, 70% MeOH in $H_2O$, 80% MeOH in $H_2O$, and 90% MeOH in $H_2O$, with the vitelevuamide eluting in the 90% MeOH/$H_2O$ fraction. This fraction was then subjected to amino flash chromatography using Bakerbond amino, 40 μm, solid support in a 28 mm I.D.×46 mm column, with stepped gradient elution in 100% chloroform followed by 2.5% MeOH in chloroform, with 12.5 mg of vitilevuamide eluting in the 5% MeOH/$CHCl_3$ fraction.

EXAMPLE 3

In this example, vitilevuamide is purified from specimens of *Polysyncraton lithostrotum* according to the procedure of Example 1.

EXAMPLE 4

In this example, vitilevuamide is purified from specimens of *Didemnum cuculliferum* according to the procedures of Example 2.

EXAMPLE 5
High Resolution Mass Spectrometry

High resolution mass measurements of vitilevuamide prepared according to the procedures of Examples 1 or 2 were made on a ZAB-SE or a Varian MAT-731 mass spectrometer. The high resolution fast atom bombardment mass spectrum showed a protonated molecular ion at m/z 1603.811768, in good agreement with a molecular formula of $C_{77}H_{114}N_{14}O_{21}S$ (Δ1.0 mmu).

EXAMPLE 6
IR and UV Spectroscopy

Infra red (IR) spectra of vitilevuamide prepared according to the procedures of Examples 1 or 2 were recorded with a Perkin-Elmer 1600 FT spectrophotometer using a thin film of vitilevuamide on sodium chloride plates. Ultraviolet (UV) spectra were recorded with a Hewlett-Packard HP8452A spectrophotometer.

IR bands at 3280, 1652, 1558, and 1538 $cm^{-1}$ (amide I and II) were indicative of HN and carbonyl stretches for peptides. These results were further evidence that vitilevuamide is a peptide. The absence of IR bands corresponding to an ammonium ion and the presence of an ester carbonyl band at 1734 $cm^{-1}$ suggested that vitilevuamide was cyclic or had terminal end modifications. Both proved correct when the structural components of vitilevuamide accounted for all but two degrees of unsaturation required by the molecular formula.

Ultraviolet (UV) spectroscopy of vitilevuamide showed an absorption at 230 nm with an extinction coefficient of 2032. Weaker absorption maxima were observed at 210 nm (ε=1719) and 250 nm (ε=1985).

EXAMPLE 7
NMR Analysis $^1$H and $^{13}$C experiments were conducted at 500 and 200 MHz, respectively, on a Varian Unity spectrometer or an IBM AF 200 spectrometer at 200 and 50 MHz, respectively. Variable temperature studies were performed at −20, −15, −10, −5, 0, 5, 10, 15, 20, 25, 30 and 35° C. using $CD_2Cl_2$, $CDCl_3$ and $C_6D_6$. Based on these results, all chemical shifts were determined in benzene at 22° C. $^1$H chemical shifts are shown herein in ppm relative to undeuterated benzene resonance at 7.15 ppm. $^{13}$C chemical shifts are shown in ppm relative to solvent resonance at 128 ppm.

The $^{13}$C NMR spectrum of vitilevuamide contains 70 resonances, 7 of which represent two carbons each. The degenerate resonances include a carbonyl at 173.28; aromatic carbons at 130.24, 130.05, 128.89 and 128.72; and α-carbons at 57.03 and 55.51 ppm.

A DEPT (distortionless enhancement of polarization transfer) experiment, M. H. Levitt et al., 94 Chem. Phys. Lett. 540 (1983); T. T. Nahkashima et al., 57 J. Mag. Reson. 149 (1984); T. T. Nahkashima et al., 59 J. Mag. Reson. 124 (1984), established the number of protons attached to each carbon, while an HMQC (heteronuclear multiple quantum coherence) experiment, A. Bax & S. Subramanian, 69 J. Mag. Reson. 565 (1986); L. Muller, 101 J. Am. Chem. Soc. 4481 (1979), permitted assignment of the attached protons. Characteristic peptide resonances in the $^1$H NMR spectrum included 11 doublets between 10.49 and 6.40 ppm and a singlet at 10.11 attributable to amide NH protons and multiplets between 5.67 and 4.81 ppm corresponding to peptide α protons.

A DQF-COSY (double quantum filter correlated spectroscopy) experiment, U. Piantini et al., 104 J. Am. Chem. Soc. 6800 (1982); M. Rance et al., 117 Biochem. Biophys. Res. Commun. 458 (1983), established the presence of two phenylalanines, valine, threonine, serine, isoleucine, alanine, proline, dehydroalanine, two homoisoleucines and N-methyl-methoxinine residues. A characteristic feature of this peptide is an ester link between the oxygen of threonine and the carbonyl of serine. This was evident from a 3 bond correlation between the β proton of threonine (5.50 ppm) and the carbonyl of serine at 169.851 ppm in an HMBC (heteronuclear multiple bond correlation) experiment (J=8 Hz), M. F. Summers et al., 108 J. Am. Chem. Soc. 4285 (1986).

Evidence for lanthionine was derived from an HMBC experiment. The 2.01 ppm β proton of one half of the lanthionine residue showed a 3 bond connectivity to carbons at 51.02 ppm (own α carbon) and 39.67 ppm (β carbon of the second half). Similarly, the 2.58 ppm β proton of the second half of the lanthionine residue showed a three bond connectivity to the β carbon (32.07 ppm) of the first half.

The terminal succinate was detected by using a combination of DQF COSY, HMQC and HMBC. COSY and TOCSY (total correlation spectroscopy), L. Braunschweiler & R. R. Ernst, 53 J. Mag. Reson. 521 (1983); A. Bax & D. G. Davis, 53 J. Mag. Reson. 521 (1985), verified the connectivity between protons at 1.68, 3.38 ppm ($^{13}$C at 30.59 ppm) and 1.78, 2.28 ppm ($^{13}$C at 28.61 ppm). HMBC experiments showed long range coupling between the protons at 2.28 ppm and 1.78 ppm and both carbonyls at 176.87 ppm and 173.28 ppm.

Table 1 contains the complete NMR assignments for vitilevuamide.

TABLE 1

| Atom No. | δ $^{13}$C | (mult.) | δ $^1$H | (mult., J(Hz)) | HMBC correlations |
|---|---|---|---|---|---|
| N1 | | | 8.66 | (d, 8.79) | C14 |
| 1 | 170.09 | (s) | | | |
| 2 | 54.77 | (d) | 5.06 | (ddd, 2.47, 2.58, 5.05) | C13, C14 |
| 3 | 63.60 | (t) | 3.91 | (dd, 2.47, 11.48) | C13 |
| | | | 4.33 | (m) | |
| 4 | 169.32 | (s) | | | |
| 5 | 57.03 | (d) | 5.68 | (d, 5.86) | C5, C14, C51 |
| 6 | 68.05 | (t) | 4.31 | (m) | |
| 7 | 70.17 | (t) | 3.61 | (m) | |
| | | | 3.45 | (m) | |
| 8 | 58.65 | (q) | 3.09 | (s) | |
| 9 | 32.49 | (q) | 3.40 | (s) | C5 |
| OH | | | 3.77 | (d, 4.44) | |
| N3 | | | 8.12 | (d, 6.90) | C4, C35, C55 |
| 10 | 173.63 | (s) | | | |
| 11 | 56.63 | (d) | 4.42 | (m) | |
| 12 | 30.58 | (d) | 2.26 | (bm) | |
| 13 | 19.12 | (q) | 1.03 | (bm) | |
| 14 | 18.95 | (q) | 0.93 | (bm) | C35, C55, C66 |
| N4 | | | 8.09 | (d, 10.66) | C1, C45 |
| 15 | 175.07 | (s) | | | |
| 16 | 54.09 | (d) | 5.27 | (ddd, 4.46, 10.45) | |
| 17 | 42.77 | (t) | 2.29 | (bm) | C1, C54, C67 |
| | | | 1.80 | (bm) | |
| 18 | 30.29 | (d) | 2.17 | (m) | |
| 19 | 18.72 | (q) | 1.10 | (d, 6.78) | |
| 20 | 30.74 | (t) | 1.48 | (bm) | |
| | | | 1.28 | (bm) | |
| 21 | 11.55 | (q) | 0.93 | (bm) | |
| N5 | | | 10.11 | (s) | C8, C15 |
| 22 | 168.26 | (s) | | | |
| 23 | 140.21 | (s) | | | |
| 24 | 111.11 | (t) | 4.71 | (s) | C8, C15, C16 |
| | | | 4.83 | (S) | |
| N6 | | | 8.00 | (d, 5.23) | C7, C31, C48 |
| 25 | 172.49 | (s) | | | |
| 26 | 60.92 | (d) | 4.19 | (bm) | C10, C48 |
| 27 | 36.94 | (d) | 1.89 | (bm) | |
| 27 | 11.55 | (q) | 0.93 | (bm) | |
| 28 | 15.01 | (q) | 1.21 | (d, 6.76) | |
| 29 | 25.10 | (t) | 1.78 | (bm) | |
| | | | 1.31 | (bm) | |
| 30 | 10.90 | (q) | 0.84 | (bm) | |
| 31 | 172.84 | (s) | | | |
| 32 | 50.94 | (d) | 4.79 | (dd, 7.17, 9.59) | C7, C47 |
| 33 | 31.95 | (t) | 3.16 | (bs) | |
| | | | 2.01 | (dd, 15.34, 17.38) | C7 |
| 34 | 174.99 | (s) | | | |
| 35 | 61.42 | (d) | 5.16 | (dd, 7.6, 15.1) | C2, C61 |
| 36 | 29.95 | (t) | 1.94 | (bm) | C2, C44 |
| | | | 1.79 | (bm) | |
| 37 | 25.11 | (t) | 1.61 | (bm) | |
| | | | 1.44 | (bm) | C30 |
| 38 | 47.01 | (t) | 3.20 | (bm) | |
| | | | 2.35 | (bm) | |
| N9 | | | 10.49 | (d, 4.95) | C11 |
| 39 | 169.96 | (s) | | | |
| 40 | 55.40 | (d) | 4.31 | (m) | C11, C49 |
| 41 | 37.13 | (t) | 3.21 | (bm) | C13, C17, C19, C37 |
| | | | 3.05 | (bs) | C13, C17, C19, C37 |
| 42 | 136.28 | (s) | | | |
| 43 | 130.12 | (d) | 7.41 | (d, 7.38) | C23 |
| 44 | 128.89 | (d) | 7.28 | (m) | C17, C18 |
| 45 | 127.57 | (d) | 7.08 | (d, 7.37) | C19 |
| 46 | 128.89 | (d) | 7.28 | (m) | C17, C18 |
| 47 | 130.12 | (d) | 7.41 | (d, 7.38) | C23 |
| N10 | | | 8.72 | (d, 6.26) | C3, C11 |
| 48 | 170.14 | (s) | | | |

TABLE 1-continued

| Atom No. | δ $^{13}$C | (mult.) | δ $^1$H | (mult., J(Hz)) | HMBC correlations |
|---|---|---|---|---|---|
| 49 | 57.03 | (d) | 4.95 | (dd, 1.12, 6.32) | C3, C11, C27 |
| 50 | 73.25 | (d) | 5.51 | (ddd, 1.23, 5.86, 6.49) | C13 |
| 51 | 19.94 | (q) | 1.14 | (d, 6.69) | |
| N11 | | | 9.22 | (d, 9.87) | C3, C10 |
| 52 | 174.94 | (s) | | | |
| 53 | 49.81 | (d) | 5.62 | (ddd, 3.35, 10.05, 10.89) | |
| 54 | 42.29 | (t) | 1.97 | (m) | C3 |
| | | | 1.87 | (bm) | |
| 55 | 31.83 | (d) | 1.78 | (m) | |
| 56 | 13.39 | (q) | 1.15 | (d, 6.56) | |
| 57 | 27.78 | (t) | 1.93 | (bm) | |
| | | | 1.40 | (bm) | |
| 58 | 11.22 | (q) | 1.03 | (bm) | |
| N12 | | | 8.40 | (d, 10.43) | C6 |
| 59 | 171.49 | (s) | | | |
| 60 | 48.60 | (d) | 5.40 | (q, 6.7, 10.47) | |
| 61 | 30.15 | (d) | 1.35 | (bm) | C10, C43 |
| N13 | | | 6.43 | (d, 7.78) | C6, C9, C38, C50 |
| 62 | 173.28 | (s) | | | |
| 67 | 128.39 | (d) | 7.28 | (m) | |
| 68 | 127.00 | (d) | 7.10 | (d, 7.58) | |
| 69 | 128.39 | (d) | 7.28 | (m) | |
| 70 | 129.82 | (d) | 7.50 | (d, 7.38) | |
| N14 | | | 6.54 | (d, 8.22) | C6 |
| 71 | 172.54 | (s) | | | |
| 72 | 55.40 | (d) | 4.44 | (bm) | |
| 73 | 39.48 | (t) | 3.33 | (m) | |
| | | | 2.59 | (dd, 11.66, 14.21) | C2, C36, C52 |
| 74 | 173.28 | (s) | | | |
| 75 | 30.41 | (t) | 3.38 | (bm) | |
| | | | 1.86 | | |
| 76 | 28.61 | (t) | 2.29 | (bm) | |
| | | | 1.78 | (bm) | |
| 77 | 176.82 | (s) | | | |

EXAMPLE 8

Mass Spectrometry Analysis

Electrospray tandem mass spectrometry was instrumental in putting together the fragments isolated and identified via NMR. Vitilevuamide (1.2 mg in methanol) prepared according to the procedure of Examples 1 or 2 was ammoniolysed by adding 1.5 ml of saturated $NH_3$ in HPLC grade methanol. The resulting solution was chilled at 0° C. for 18 hours. The resulting mixture was then subjected to reverse phase HPLC in a Waters NOVAPAK $C_{18}$ column (4.6×100 mm) with isocratic elution in 90% MeOH/$H_2$O to isolate the partially linear peptide. Mild acidic or basic hydrolysis of vitilevuamide to cleave the deydroamino acid unit gave very poor yields of the corresponding partially linear peptide and resulted in decomposition.

The partially linear peptide was analyzed by electrospray mass spectrometry on a Fissons Trio 2000 electrospray mass spectrometer, which established a molecular formula of 1620.8, in good agreement (after subtracting the mass of ammonia, m/z=17) with the mass determined in Example 5.

EXAMPLE 9

The partially linearized molecule of Example 8 was subjected to tandem mass spectroscopy for sequential analysis. Tandem mass spectroscopy (MS/MS) was performed on the SIAX API III spectrometer. Five $\mu$l of sample was dissolved in 190 $\mu$l of $H_2O$:$CH_3OH$:$CH_3COOH$ (50:50:1) at a flow rate of 2 $\mu$l/min.

Figure 2:
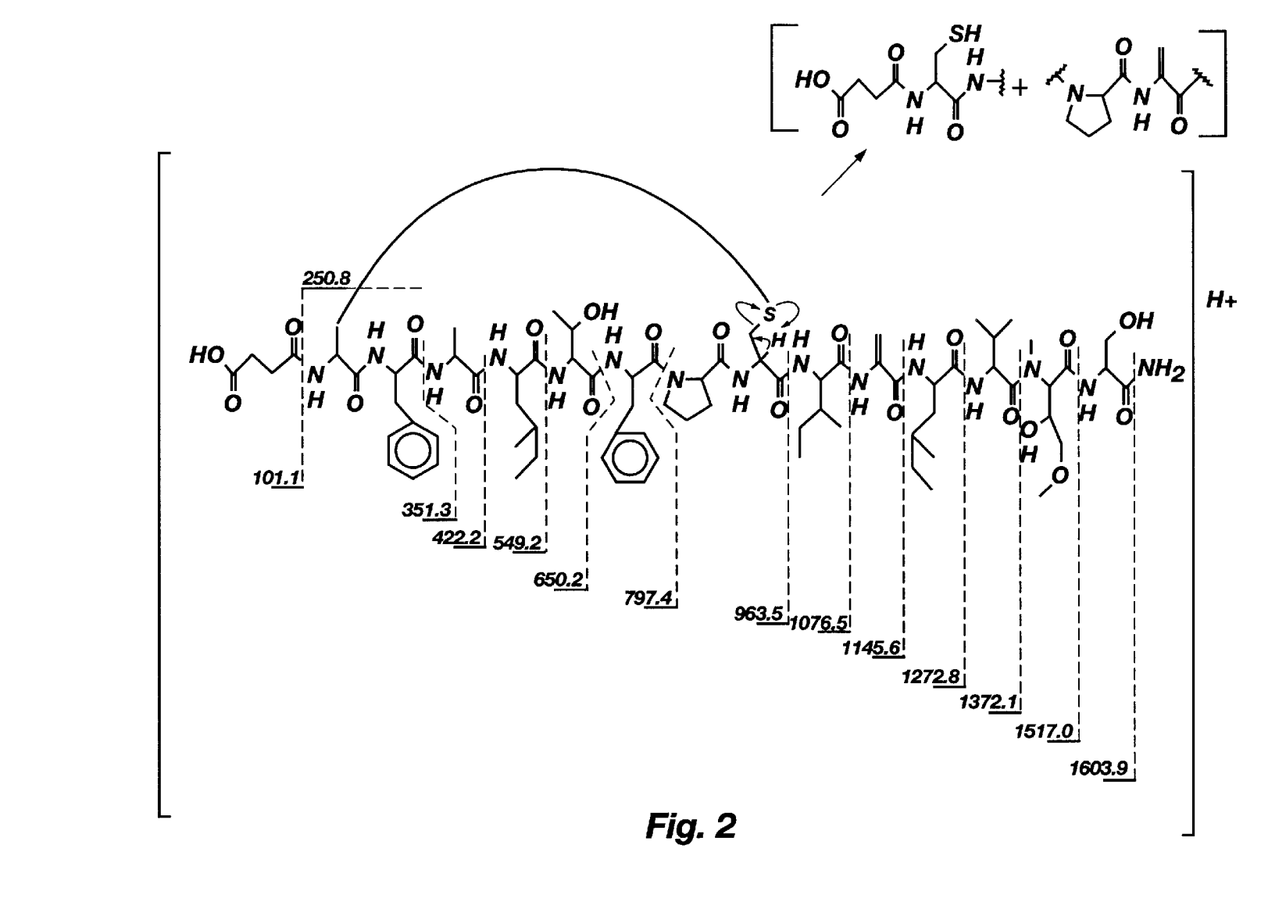
FIG. 2 shows the major fragmentation pattern of vitilevuamide upon tandem mass spectroscopy for sequential analysis.

The major fragmentation pattern (FIG. 2) shows sequential losses from the amidated C-terminus to produce massto-charge ratios (m/z) of 1603.9, 1518, 1372.1, 1272.8, 1145.6, 1076.5, and 963.5. These results correspond with the successive losses of ammonia (m/z=17), Ser (m/z=87), N-methyl methoxinine (Nmm; m/z=145), Val (m/z=99), homoisoleucine (Hil; m/z=127), dehydroalanine (Dha; m/z=69), and Ile (m/z=113).

Subsequent fragmentation occurs after a rearrangement resulting in the loss of 166 mass units formed by proline and part of the lanthionine (Lan) residue. The Lan residue is eliminated in the form of dehydroalanine to give an m/z of 797.4. A. G. Craig, 20 Biological Mass. Spec. 195 (1991). The cleavage of the Lan bridge occurs with a transfer of a pair of electrons from the electron-rich sulfur atom to the α-proton of Lan 7. This results in breaking of the sulfur bridge between Lan and the formation of a Dha residue instead of Lan 7. This sulfur is retained by Lan 14 as a thiol yielding cysteine in subsequent cleavages.

The fragmentation continues with the subsequent loss of amino acids resulting in m/z of 650.2, 549.2, 422.2, and 351.3, corresponding to loss of Phe (m/z=147), Thr (m/z=101), Hil (m/z=127), and Ala (m/z=71). The next loss of 250 units is a coupled loss of phenylalanine and cysteine, leaving the terminal succinate fragment of 101 mass units. Throughout the spectrum the loss of 18 units (i.e. $H_2O$) is observed.

EXAMPLE 10
Assignment of Hil

Two, 2-amino-4-methylhexanoic acid (homoisoleucine, Hil) units were identified after analyzing the PS (phase sensitive) DQF COSY and TOCSY spectra of vitilevuamide. The stereochemistry of the amino acids was confirmed by chemical synthesis of all four diastereomers, and evaluation of the 1-fluoro-2,4-dinitrophenyl-5-L-alanineamide (FDAA; Sigma Chemical Co., St. Louis, Mo.) derived amino acids by HPLC on a cyano column. The mixtures of (2RS,4S) and all four isomers of Hil were synthesized starting from S-(+) and (±)-1-bromo-2-methyl butane (Sigma Chemical Co. or Aldrich Chemical Co., Milwaukee, Wis.) respectively using the method of H. Han & R. A. Pascal, 55 J. Org. Chem. 5173 (1990). The diastereomeric mixture of (2RS,4S)-2-amino-4-methyl hexanoic acid was treated with catalase and L-amino acid oxidase (Aldrich Chemical Co.) at pH 8 for 12–18 hours. Upon acidification and reverse phase chromatography (9:1, MeOH/$H_2O$), the pure (2R,4S) isomer of Hil was isolated. Using these standards it was possible to verify the stereochemistry of the two Hil residues in vitilevuamide by FDAA derivatization and cyano HPLC chromatography (MeOH/1% Acetic acid, 25:75–90:10 at 1 mL/min) with UV detection at 340 nm.

EXAMPLE 11
Assignment of N-methyl-methoxinine

The $^1H$ NMR signals of the unknown amino acid ($C_6H_{11}O_3N$, 143 da) were assigned by using TOCSY and DQF COSY. COSY connectivity between 5.66 ppm (α proton), 4.66 ppm (β proton) and 3.59, 3.43 ppm (diastereotopic δ protons) established the basic structure. The presence of the N- and O-methyl group was confirmed by HMBC connectivity between the methyl singlets at 3.38 and 3.06 to the α and δ carbons respectively.

Nmm was synthesized through the intermediate 3-methoxy-2-hydroxypropionaldehyde (3-O-methylglyceraldehyde). This aldehyde was prepared by the procedure of J. R. Durrwachter et al., 108 J. Am. Chem. Soc. 7812 (1986), at a yield of 47%. NMR results were consistent with published data. This aldehyde was converted to 2-aminomethyl-3-hydroxy-4-methoxybutane nitrile by addition of methylamine in an alkaline medium followed by addition of potassium cyanide (80% yield). The structure of this nitrile was also confirmed by NMR. The nitrile was then subjected to acid hydrolysis, resulting in Nmm (58% yield). This procedure resulted in synthesis of all isomers. Proton and carbon-13 NMR data were obtained.

EXAMPLE 12
Stereochemistry of Amino Acids in Vitilevuamide

The stereochemistry of many amino acids can be determined by reverse phase HPLC after derivatization with FDAA (1-fluoro-2,4-dinitrophenyl-5-L-alanine-amide). P. Marfey, 49 Carlsberg Res. Commun. 591 (1984); J. G. Adamson et al., 202 Anal. Chem. 210 (1992).

Hydrolysis of vitilevuamide prepared according to the procedure of Example 1 or Example 2 was carried out in 5 mL of 6N HCl under a nitrogen atmosphere in a sealed bomb at 108° C. for 22 hours. After traces of HCl were removed by repeated evaporation in vacuo, the residual hydrolysate was suspended in 500 µl of water and derivatised with (1-fluoro-2,4-dinitrophen-5-yl)L-alanineamide (FDAA). HPLC analysis (Waters NOVAPAK $C_{18}$; 4.6×100 mm column, linear gradient elution, triethylammonium phosphate (50 mM, pH 3.0)/acetonitrile, 90:10–60:40 in 45 mins; 1.0 mL/min; UV detection at 340 nm) of FDAA-derivatized amino acid standards (Sigma Chemical Co.) coinjected with the vitilevuamide hydrolysate established the stereochemistry of the constituent amino acids with the exception of homoisoleucine, lanthionine, and N-methyl methoxinine.

The conditions for the stereochemistry determination of isoleucine included gradient cyano HPLC (Rainin Microsorb, 4.6×250 mm, at MeOH/1% acetic acid, 35:65–42:58 for 30 mins at 1 mL/min with UV detection at 340 nm. For homoisoleucine, similar conditions were used except that a linear gradient of 25% MeOH to 90% MeOH for 50 minutes at a flow rate of 1 mL/min was used.

These experiments established the presence of D-allo-threonine, D-valine, D-phenylalanine, D-alanine, L-serine, L-proline, L-isoleucine, D-allo-homoisoleucine, and L-homoisoleucine.

EXAMPLE 13
Toxicity Testing in Hunan Tumor Cell Lines

Vitilevuamide prepared according to the procedure of Example 1 or Example 2 was tested against a panel of human tumor cell lines: (a) a colon cancer cell line, HCT 116 (obtained from ATCC), M. Brattain, 41 Cancer Res. 1751 (1986); (b) an adenocarcinoma cell line, A549, D. J. Giard, 51 J. Nat'l Cancer Inst. 1417 (1973); (c) a malignant melanoma cell line, SK-MEL-5, H. F Oteggen, 41 J. Nat'l Cancer Inst. 827 (1968); and (d) a kidney carcinoma cell line, A498, S. Aaronson, 51 J. Nat'l Cancer Inst. 1417 (1973). Cells were cultured according to the procedure of M. C. Alley et al., 48 Cancer Res. 589 (1988), hereby incorporated by reference.

Screening was performed in a 96-well microtiter plate by the standard 3-[4,5-dimethylthiazol-2-yl]-2,5-phenyltetrazolium bromide; thiazolyl blue (MTT) cell inhibition assay adopted for anticancer drug screening at NIH. J. Carmichael et al., 47 Cancer Res. 936 (1987), hereby incorporated by reference. Positive controls were run simultaneously.

Figure 3:
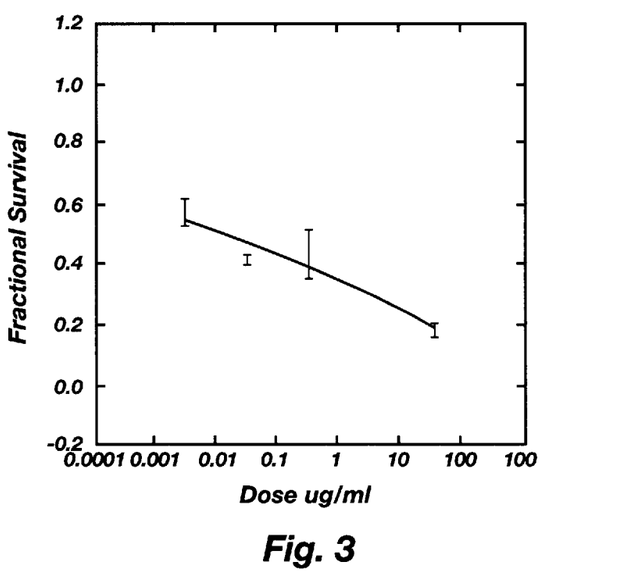
FIG. 3 shows the fractional survival of HCT 116 tumor cells as a function of dose of vitilevuamide.
Figure 4:
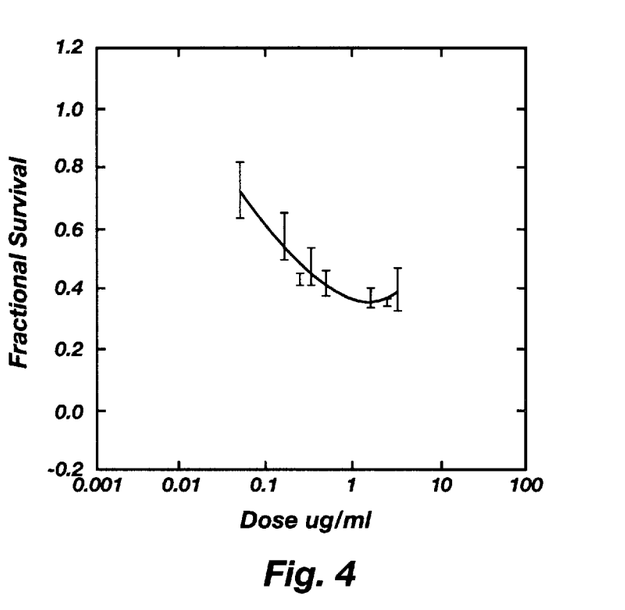
FIG. 4 shows the fractional survival of A549 tumor cells as a function of dose of vitilevuamide.
Figure 5:
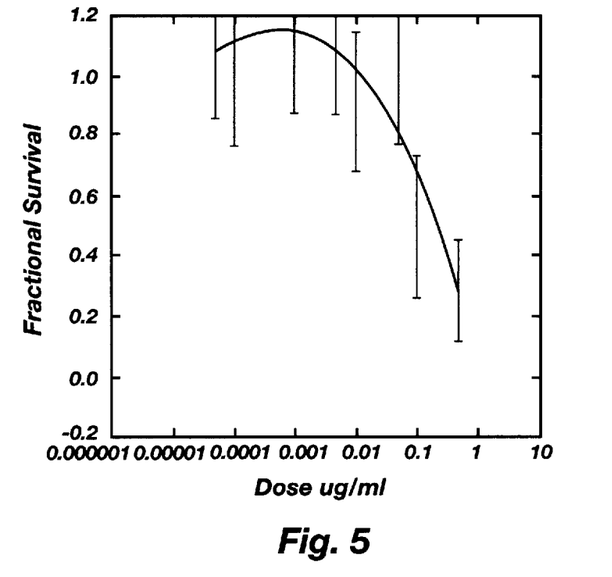
FIG. 5 shows the fractional survival of SK-MEL-5 tumor cells as a function of dose of vitilevuamide.
Figure 6:
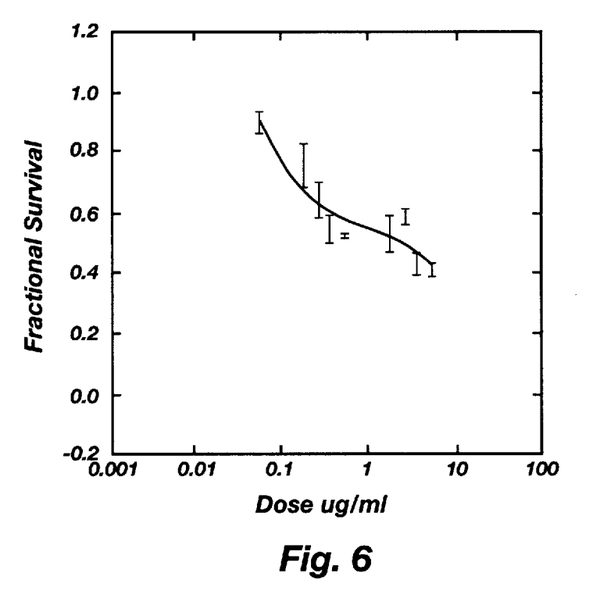
FIG. 6 shows the fractional survival of A498 tumor cells as a function of dose of vitilevuamide.

Vitilevuamide was strongly cytotoxic against all of the cell lines tested, exhibiting 50% inhibitory concentrations ($IC_{50}$) as follows: 10 ng/mL in HCT 116 cells (FIG. 3); 0.2 µg/mL in A549 cells (FIG. 4); 0.5 µg/mL in SK-MEL-5 cells (FIG. 5); and 5 µg/mL in A498 cells (FIG. 6). Thus, vitilevuamide is an antitumor agent according to this test viewed by those skilled in the art as reasonably predictive thereof.

EXAMPLE 14
Tubulin Inhibition Assay

C6 rat glioma cells (ATCC CCL107) were seeded into the wells of a microtiter plate and then incubated for 1 day. The cells were then treated with a range of vitilevuamide concentrations, normally 5 orders of magnitude, and incubated for 4 additional hours. The cells were then treated for 1 hour with 1 mM dibuteryl-cAMP (db-cAMP), which causes the C6 cells to assume a spherical morphology ("rounding") within 60 minutes due to polymerization of tubulin. Cells that are exposed to tubulin-active compounds, on the other hand, display a different morphological change—flattening and adherence to the substrate. All of the wells were then jet aspirated, and the wells were resupplied with fresh medium containing MTT. The glioma cells metabolize MTT to a dark formazan dye. P. R. Twentyman & M. Luscombe, 56 Br. J. Cancer 279 (1987); F. Denizot & R. Lang, 89 J. Immunol. Methods 271 (1986). Following 4 hours of incubation, absorbance was measured at 450 nm. Colchicine (25 $\mu$g/mL) was used as the positive control.

Figure 7:
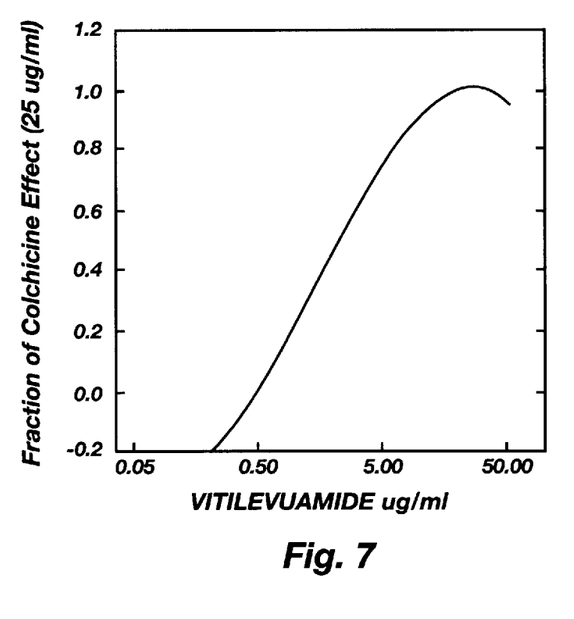
FIG. 7 shows the absorbance of C6 rat glioma cells treated with vitilevuamide expressed as a function of the absorbance of such cells treated with 25 µg/mL of colchicine.

In this assay, vitilevuamide showed the same effect as colchicine at a concentration of 4 $\mu$g/mL. FIG. 7 shows the absorbance of wells treated with vitilevuamide expressed as a function of the absorbance of wells treated with 25 $\mu$g/mL of colchicine. These results show that the antitumor activity of vitilevuamide is likely due to interaction with the microtubule system.

EXAMPLE 15

Vitilevuamide was also screened for in vivo activity by injecting CDF1 mice intraperitoneally on day 0 with $1\times10^6$ P388 tumor cells. Five animals were randomly assigned to a group. On days 1, 5, and 9 after tumor implantation, these mice were treated intraperitoneally with either a placebo or the drug. Animals were checked twice daily, and the day of death of each mouse was recorded. A positive drug response is defined as a greater than 25% increase in the mean life span (% ILS) relative to the placebo control. The results of this experiment are shown in Table 2.

TABLE 2

| Dose (mg/kg/dose) | % ILS |
|---|---|
| 0.13 | −45 (toxic) |
| 0.06 | −13 (toxic) |
| 0.03 | 70 |
| 0.012 | 20 |
| 0.006 | 8 |

These results show that vitilevuamide exhibited a % ISL of 70 at a dose of 0.03 mg/kg. Thus, vitilevuamide is an antitumor agent according to this test viewed by those skilled in the art as reasonably predictive thereof.

We claim:

1. A purified compound selected from the group consisting of vitilevuamide and pharmaceutically acceptable salts thereof.

2. The purified compound of claim 1 wherein said compound is vitilevuamide.

3. A composition for treating cancer comprising an effective amount of an anticancer agent selected from the group consisting of vitilevuamide, pharmaceutically acceptable salts thereof, and mixtures thereof; and an inert carrier.

4. The composition of claim 3 wherein said anticancer agent is vitilevuamide.

5. The composition of claim 4 further comprising a member selected from the group consisting of excipients, wetting agents, emulsifying agents, and buffers.

6. A method for purifying vitilevuamide comprising the steps of:
(a) collecting specimens of an ascidian selected from the group consisting of *Didemnum cuculliferum* and *Polysyncraton lithostrotum;*
(b) repeatedly extracting said specimens with methanol to yield a crude homogenate;
(c) separating said crude homogenate into fractions of increasing polarity by extracting first with hexanes and then with chloroform to yield a chloroform extract;
(d) subjecting said chloroform extract to a first silica gel flash chromatography step with stepped gradient elution with chloroform, 99:1 chloroform/methanol, and then 98:2 chloroform/methanol to obtain a 98:2 chloroform/methanol eluant;
(e) subjecting said 98:2 chloroform/methanol eluant to a second silica gel flash chromatography step with stepped gradient elution with 3:7 acetone/hexanes, and then 7:3 acetone/hexanes to yield a 7:3 acetone/hexanes fraction; and
(f) subjecting said 7:3 acetone/hexanes fraction to reverse phase HPLC with a mobile phase of 9:1 $CH_3CN/H_2O$ such that a fraction is separated therefrom comprising a bicyclic peptide with a molecular weight of about 1603.8.

7. The method of claim 6 wherein said ascidian is *Didemnum cuculliferum*.

8. The method of claim 7 wherein said ascidian is *Polysyncraton lithostratum*.

9. A method for purifying vitilevuamide comprising the steps of:
(a) collecting specimens of an ascidian selected from the group consisting of *Didemnum cuculliferum* and *Polysyncraton lithostrotum;*
(b) repeatedly extracting said specimens with methanol to yield a crude homogenate;
(c) separating said crude homogenate into fractions of increasing polarity by extracting first with hexanes and then with chloroform to yield a chloroform extract;
(d) subjecting said chloroform extract to silica gel flash chromatography with stepped gradient elution with chloroform, 99:1 chloroform/methanol, and then 98:2 chloroform/methanol to obtain a 98:2 chloroform/ methanol eluant;
(e) subjecting said 98:2 chloroform/methanol eluant to reverse phase flash chromatography with stepped gradient elution with $H_2O$, 50% methanol/$H_2O$, 70% methanol/$H_2O$, 80% methanol/$H_2O$, and 90% methanol/$H_2O$ to obtain a 90% methanol/$H_2O$ eluant; and
(f) subjecting said 90% methanol/$H_2O$ eluant to amino flash chromatograph with stepped gradient elution with chloroform and then 2.5% methanol/chloroform to obtain a 2.5% methanol/chloroform eluant comprising a bicyclic peptide with a molecular weight of about 1603.8.

10. The method of claim 9 wherein said ascidian is *Didemnum cuculliferum*.

11. The method of claim 9 wherein said ascidian is *Polysyncraton lithostratum*.

12. A compound purified from *Didemnum cuculliferum* or *Polysyncraton lithostrotum* by a process comprising the steps of:
(a) collecting specimens of an ascidian selected from the group consisting of *Didemnum cuculliferum* and *Polysyncraton lithostrotum;*

(b) repeatedly extracting said specimens with methanol to yield a crude homogenate;

(c) separating said crude homogenate into fractions of increasing polarity by extracting first with hexanes and then with chloroform to yield a chloroform extract;

(d) subjecting said chloroform extract to a first silica gel flash chromatography step with stepped gradient elution with chloroform, 99:1 chloroform/methanol, and then 98:2 chloroform/methanol to obtain a 98:2 chloroform/methanol eluant;

(e) subjecting said 98:2 chloroform/methanol eluant to a second silica gel flash chromatography step with stepped gradient elution with 3:7 acetone/hexanes, and then 7:3 acetone/hexanes to yield a 7:3 acetone/hexanes fraction; and (f) subjecting said 7:3 acetone/hexanes fraction to reverse phase HPLC with a mobile phase of 9:1 $CH_3CN/H_2O$ such that a fraction is separated therefrom comprising a bicyclic peptide with a molecular weight of about 1603.8.

13. A compound purified from *Didemnum cuculliferum* or *Polysyncraton lithostrotum* by a process comprising the steps of:

(a) collecting specimens of an ascidian selected from the group consisting of *Didemnum cuculliferum* and *Polysyncraton lithostrotum*;

(b) repeatedly extracting said specimens with methanol to yield a crude homogenate;

(c) separating said crude homogenate into fractions of increasing polarity by extracting first with hexanes and then with chloroform to yield a chloroform extract;

(d) subjecting said chloroform extract to silica gel flash chromatography with stepped gradient elution with chloroform, 99:1 chloroform/methanol, and then 98:2 chloroform/methanol to obtain a 98:2 chloroform/methanol eluant;

(e) subjecting said 98:2 chloroform/methanol eluant to reverse phase flash chromatography with stepped gradient elution with $H_2O$, 50% methanol/$H_2O$, 70% methanol/$H_2O$, 80% methanol/$H_2O$, and 90% methanol/$H_2O$ to obtain a 90% methanol/$H_2O$ eluant; and (f) subjecting said 90% methanol/$H_2O$ eluant to amino flash chromatograph with stepped gradient elution with chloroform and then 2.5% methanol/chloroform to obtain a 2.5% methanol/chloroform eluant comprising a bicyclic peptide with a molecular weight of about 1603.8.

14. A method for treating cancer in an individual in need of such treatment comprising administering a composition comprising an effective amount of an anticancer agent selected from the group consisting of vitilevuamide, pharmaceutically acceptable salts thereof, and mixtures thereof; and an inert carrier.

15. The method of claim 14 wherein said anticancer agent is vitilevuamide.

16. The method of claim 15 further comprising a member selected from the group consisting of excipients, wetting agents, emulsifying agents, and buffers.

17. The method of claim 14 wherein said composition is administered by systemic administration.

* * * * *